US00PP21612P2

(12) United States Plant Patent
Meilland

(10) Patent No.: US PP21,612 P2
(45) Date of Patent: Jan. 11, 2011

(54) SHRUB ROSE PLANT NAMED 'MEISWETDOM'

(50) Latin Name: *Rosa hybrida*
Varietal Denomination: Meiswetdom

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/585,531

(22) Filed: Sep. 17, 2009

(51) Int. Cl.
*A01H 5/00* (2006.01)

(52) U.S. Cl. ..... Plt./107

(58) Field of Classification Search ..... Plt./107
See application file for complete search history.

*Primary Examiner*—Annette H Para
(74) *Attorney, Agent, or Firm*—Buchanan Intersoll & Rooney PC

(57) ABSTRACT

A new and distinct variety of Shrub rose plant is provided that forms in clusters in abundance on a substantially continuous basis attractive double medium pink cup-shaped blossoms that clean well upon full maturity. The buds are rounded to bluntly pointed in shape. A vigorous spreading ground cover growth habit is displayed. The disease resistance is excellent with respect to Black Spot, Powdery Mildew, and Rust. The plant develops well regardless of the mode of asexual propagation. The plant is particularly well suited for growing in small areas as a ground cover, as a mass planting, and in containers where attractive ornamentation is desired.

2 Drawing Sheets

Botanical/commercial classification: *Rosa hybrida*/Shrub Rose Plant.

Varietal denomination: cv. Meiswetdom.

SUMMARY OF THE INVENTION

The new variety of *Rosa hybrida* Shrub rose plant was created during June 1998 in France by artificial pollination wherein two parents were crossed which previously had been studied in the hope that they would contribute the desired characteristics. The female parent (i.e., the seed parent) was an unnamed seedling (non-patented in the United States). The male parent (i.e., the pollen parent) was 'The Fairy' variety (non-patented in the United States).

The parentage of the new variety can be summarized as follows:

Unnamed Seedling×'The Fairy'.

The seeds resulting from the above pollination were sown and small plants were obtained which were physically and biologically different from each other. Selective study resulted in the identification of a single plant of the new variety.

It was found that the new Shrub rose plant of the present invention:

(a) displays a vigorous spreading ground cover growth habit, (b) abundantly forms in clusters on a substantially continuous basis attractive double cup-shaped medium pink blossoms that clean well upon full maturity, (c) displays attractive semi-glossy medium green foliage that contrasts well with the blossom coloration, (d) develops well following asexual propagation, (e) resistant to Black Spot, Powdery Mildew, and Rust, and (f) is particularly well suited for providing attractive ornamentation as a mass planting and when grown in containers.

The new variety well meets the needs of the horticultural industry and can be grown to advantage as ornamentation in parks, gardens, public areas, and in residential settings where attractive ornamentation is desired as a ground cover, as a mass planting, and in containers.

The new variety can be readily distinguished from its ancestors and other Shrub rose varieties. 'The Fairy' variety displays a significantly smaller stature and is more compact. Also, the new variety can be distinguished from the 'Meigalpio' variety (U.S. Plant Pat. No. 17,877), the 'Meijocos' variety (U.S. Plant Pat. No. 18,874), the 'Meiggili' variety (U.S. Plant Pat. No. 18,542), and the 'Meidrifora' variety (U.S. Plant Pat. No. 19,148). The 'Meigalpio' variety forms small brilliant red-pink blossoms, the 'Meijocos' forms deep pink blossoms with fewer petals, the 'Meiggili' variety forms bright peach colored blossoms, and the 'Meidrifora' variety forms deep coral-orange blossoms.

The new variety has been found to undergo asexual propagation at Wasco, Calif., U.S.A., and near West Grove, Pa., U.S.A., by a number of routes, including budding, grafting, and the use of cuttings. Such asexual propagation by the above-mentioned techniques has shown that the characteristics of the new variety are stable and are strictly transmissible by such asexual propagation from one generation to another. Accordingly, the new variety undergoes asexual propagation in a true-to-type manner. The plant development is particularly good regardless of the mode of asexual propagation.

The new variety has been named 'Meiswetdom', and is being marketed under the SWEET DRIFT trademark.

BRIEF DESCRIPTION OF THE PHOTOGRAPHS

The accompanying photographs show, as nearly true as it is reasonably possible to make the same in color illustrations of this character, typical flowering rose plants of the new variety. The illustrated plants were approximately three years of age and were observed during July 2009 while growing on their own roots in a field near West Grove, Pa., U.S.A.

DETAILED DESCRIPTION

Figure 1:
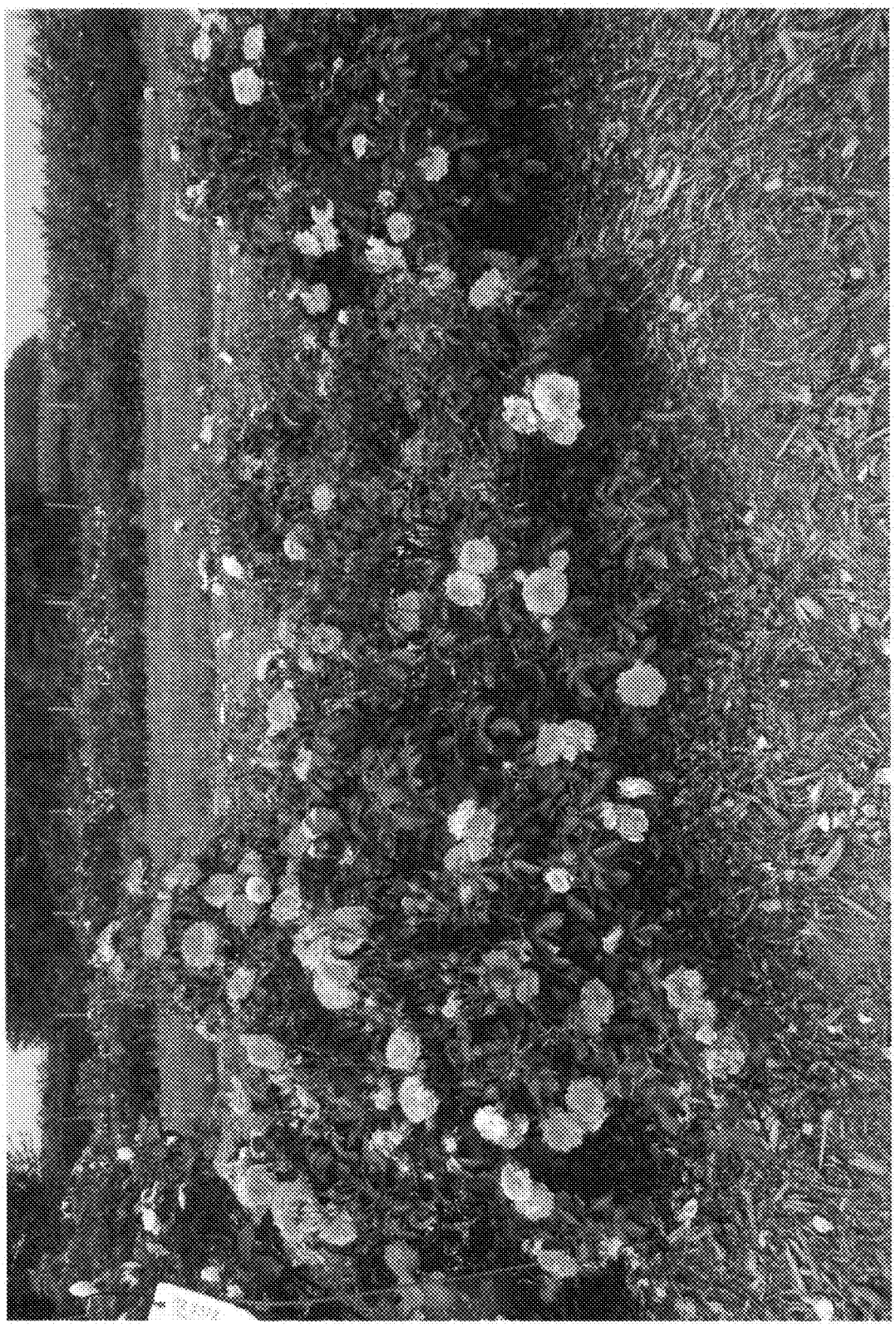
FIG. 1 illustrates a row of plants of the new variety wherein the spreading ground cover growth habit is illustrated.
Figure 2:
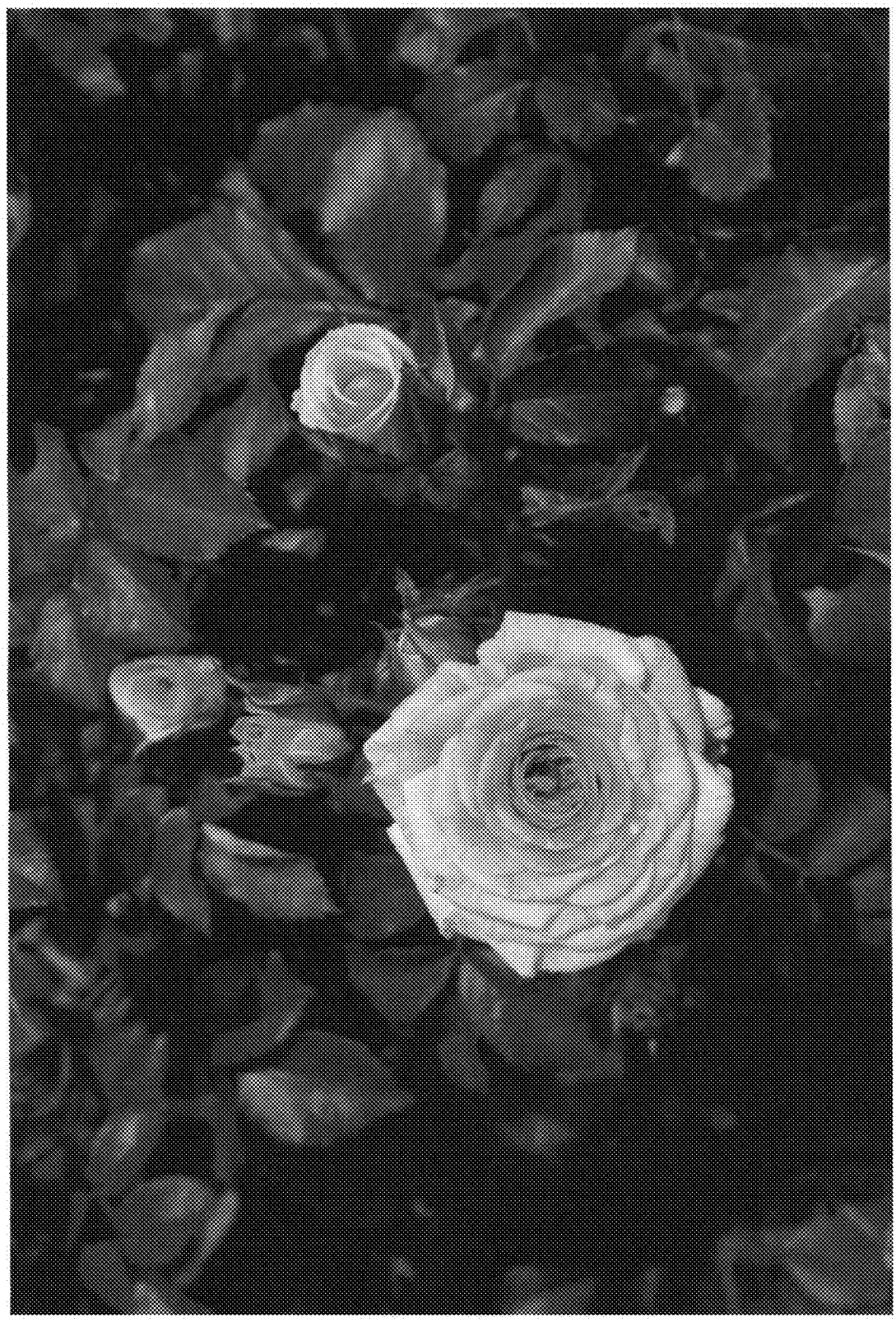
FIG. 2 illustrates a close view of the flowers in various stages of development as well as the foliage.

The chart used in the identification of the colors is that of The Royal Horticultural Society (R.H.S. Colour Chart) except where ordinary color terms are utilized. Such common color terms are to be accorded their customary dictionary significance. The description is based upon the observation of a plant of the new variety at an age of approximately three years during the month of July while being grown outdoors on its own roots near West Grove, Pa., U.S.A.

Class: Landscape Shrub Rose.

Plant:

*Growth habit.*—Suitable for a ground cover, spreading, low, and rounded.

*Blooming habit.*—Substantially continuous.

*Height.*—Commonly approximately 60 cm on average at the end of the growing season.

*Width.*—Commonly approximately 75 cm on average at the end of the growing season.

Branches:

*Color.*—Young stems: commonly between Green Group 137C and 137D. Adult wood: commonly near Green Group 137A.

*Thorns.*—Size: commonly approximately 1.0 cm in length on average on young stems, and approximately 4 mm in length on average on mature stems. Configuration: commonly sharply pointed with the tip nearly perpendicular to the stem and pointing downwards. Quantity: typically approximately 16 on average over a stem length of 20 cm. Color: Greyed-Yellow Group 160B on young stems, and between Greyed-Orange Group 166C and 166D on mature stems.

Leaves:

*Length.*—Commonly approximately 11 cm on average including the petiole for a mature five-leaflet leaf, and commonly approximately 9 cm on average including the petiole for a mature seven-leaflet leaf.

*Width.*—Commonly approximately 8 cm on average at the widest point for a mature five-leaflet leaf, and commonly approximately 5 cm on average at the widest point for a mature seven-leaflet leaf.

*Leaflets.*—Arrangement: alternate and pinnate. Number: 5, 7 (more typically), and 9 (rarely). Shape: generally elliptical to broadly elliptical. Apex: commonly broadly acute to rounded. Base: commonly short attenuate. Margins: serrulate. Texture: glabrous on the upper and under surfaces. General appearance: small, dense, medium green, and semi-glossy. Color (young foliage): on the upper surface near Yellow-Green Group 146B with margins near Greyed-Purple Group 183A, and on the under surface near Yellow-Green Group 146B with margins near Greyed-Red Group 181A. Color (adult foliage): on the upper surface near Yellow-Green Group 147A, and on the under surface near Green Group 139C.

*Stipules.*—Length: commonly approximately 15 mm on average. Width: commonly approximately 7 mm on average. Color: commonly near Yellow-Green Group 145A with edges of near Yellow-Green Group 147A.

*Petioles.*—Length: commonly approximately 2 cm on average. Diameter: commonly approximately 2 mm on average. Color: near Yellow-Green Group 144A.

Inflorescence:

*Bearing.*—Commonly in clusters of 3 to 5 flowers.

*Peduncle.*—Commonly approximately 2.5 cm in length on average, and approximately 2 mm in diameter on average.

*Sepals.*—Number 5. Length: commonly approximately 1.5 cm on average. Width: commonly approximately 6 mm on average. Color: near Green Group 143A on the inner and outer surfaces.

*Buds.*—shape: rounded to bluntly pointed. Size: small. Length: approximately 1.5 cm on average as the calyx breaks. Width: approximately 1 cm at the widest point on average as the calyx breaks. color: as the bud cracks, the petals are near Red-Purple Group 58C on the upper and under surfaces.

*Flower.*—Shape: cup-shaped when fully open. Diameter: approximately 4.5 to 5 cm on average when fully open. Color (newly opened): on both surfaces the outer petals are near Red Group 36B on the outer edges and near Red Group 36D towards the point of attachment, and the inner petals are near Red Group 55A on the outer edges and near Yellow Group 11D towards the point of attachment. Color (fully open): on both surfaces the outer edges are near Red Group 48D and near Yellow Group 2D towards the point of attachment. Color stability: color darkens some with progress towards full maturity. Fragrance: none. Petal number: approximately 90 to 100 on average under normal growing conditions. Petal shape: obovate to narrowly obovate to narrowly obcordate. Petal apex: obtuse. Petal base: narrowly cuneate. Petal size: outer petals commonly are approximately 2 cm in length on average and approximately 1.5 cm in width on average, and inner petals commonly are approximately 1.5 cm in length on average and approximately 1 cm in width on average. Petal texture: glabrous, membranaceous, relatively thin, and semi-transparent. Petal margin: entire and slightly revolate. Petal arrangement: imbricated. Petal drop: very good with the petals commonly detaching cleanly before drying. Stamen number: approximately 30 to 35 on average. Filaments: commonly approximately 6 mm in length on average, and approximately 1 mm in diameter. Pollen: near Yellow-Orange Group 22A in coloration. Pistils: approximately 30 on average. Styles: commonly approximately 6 mm in length on average, and less than 1 mm in diameter on average. Lasting quality: the blossoms commonly last approximately 7 to 8 days on the plant, and approximately 5 days when cut and placed in a vase. Receptacle: slightly glaucous, commonly approximately 2.5 to 2.8 mm in size when the flower is completely open, and near Green Group 138A in coloration.

Development:

*Vegetation.*—Vigorous and procumbent relatively thin branches with upright thin shoots and generally restrained growth.

*Blooming.*—Abundant and substantially continuous.

*Tolerance to diseases.*—Excellent with respect to Black Spot, Downy Mildew, Powdery Mildew, and Rust.

*Formation of hips/seeds.*—Sparse.

*Hardiness.*—U.S.D.A. Hardiness Zone No. 5.

I claim:

1. A new and distinct Shrub rose plant characterized by the following characteristics:

(a) displays a vigorous spreading ground cover growth habit, (b) abundantly forms in clusters on a substantially continuous basis attractive double cup-shaped medium pink blossoms that clean well upon full maturity, (c) displays attractive semi-glossy medium green foliage that contrasts well with the blossom coloration, (d) develops well following asexual propagation, (e) is resistant to Black Spot, Powdery Mildew, and Rust, and (f) is particularly well suited for providing attractive ornamentation as a mass planting and when grown in containers;

substantially as shown and described.

* * * * *